United States Patent [19]

Fiorini et al.

[11] Patent Number: 5,128,373
[45] Date of Patent: Jul. 7, 1992

[54] PACKAGES CONTAINING INJECTABLE FORMULATIONS OF THE SODIUM SALT OF NAPROXEN

[75] Inventors: Roberta Fiorini, Bologna; Egidio Marchi, Casalecchio di Reno, both of Italy

[73] Assignee: Alfa Wassermann S.p.A., Alanno Scalo, Italy

[21] Appl. No.: 679,113

[22] Filed: Apr. 2, 1991

Related U.S. Application Data

[62] Division of Ser. No. 622,925, Dec. 6, 1990, Pat. No. 5,096,926.

[30] Foreign Application Priority Data

Apr. 17, 1990 [IT] Italy ................................ 3452 A/90

[51] Int. Cl.⁵ ............................................ A61K 31/19
[52] U.S. Cl. ................................... 514/569; 206/328
[58] Field of Search ................. 514/557, 569; 206/328

[56] References Cited

U.S. PATENT DOCUMENTS

| | | | |
|---|---|---|---|
| 4,501,360 | 2/1985 | Levy et al. | 206/443 |
| 4,593,044 | 6/1986 | Metz | 514/557 |
| 4,799,590 | 1/1989 | Furman | 206/390 |
| 4,936,314 | 6/1990 | Kasai et al. | 128/764 |

*Primary Examiner*—Frederick E. Waddell
*Assistant Examiner*—Diane Gardner
*Attorney, Agent, or Firm*—Bucknam and Archer

[57] ABSTRACT

Aqueous stable injectable formulations containing the sodium salt of naproxen, stabilizing agents and polyhydroxylic alcohols, packaged in containers made up of boxes of polystyrene or of an equivalent material covered with films which absorb the light radiations.

7 Claims, 1 Drawing Sheet

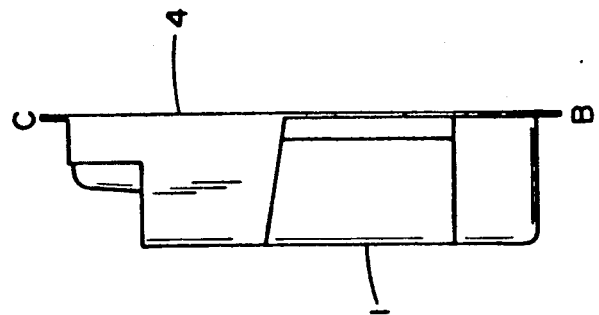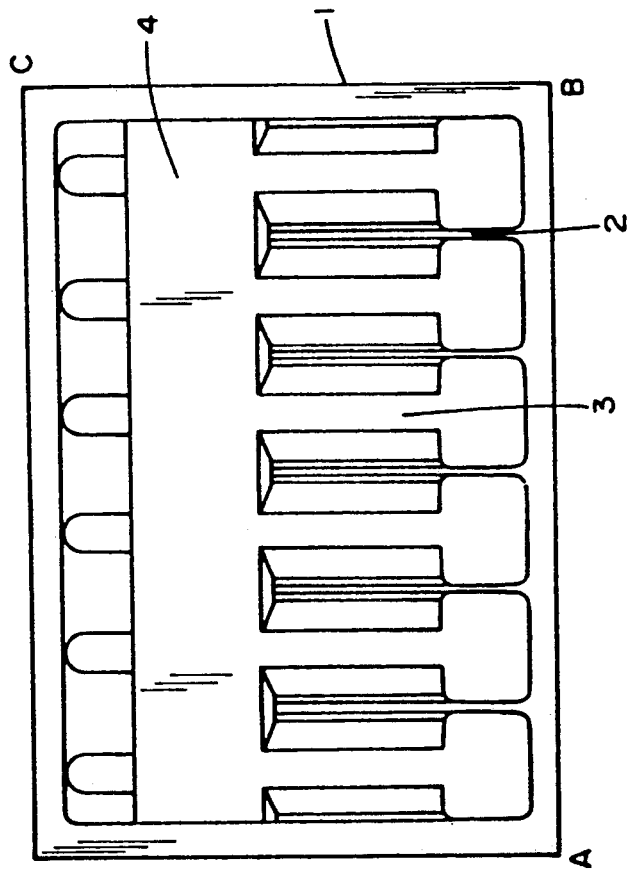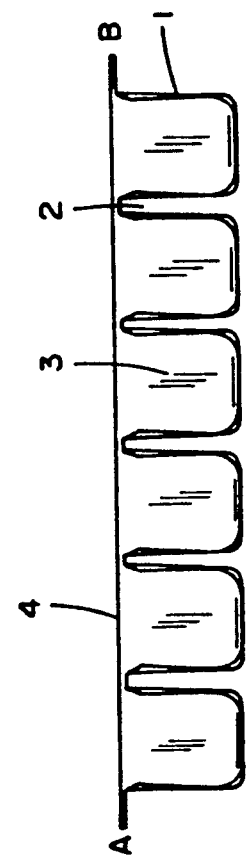

PACKAGES CONTAINING INJECTABLE FORMULATIONS OF THE SODIUM SALT OF NAPROXEN

This is a divisional of application Ser. No. 622,925, filed Dec. 6, 1990, now U.S. Pat. No. 5,096,926.

BACKGROUND OF THE INVENTION

The method of parenteral administration is known to be useful in helping the absorption of many drugs and, among them, also of the non-steroidal anti-inflammatory drugs.

The sodium salt of naproxen, among these, a drug universally known for its valued analgesic, antipyretic and anti-inflammatory activities, has a remarkable importance.

The possibility to use the sodium salt of the naproxen for injectable use was limited till now by the poor stability to the heat and light of its aqueous solutions.

As a matter of fact, aqueous solutions containing the sodium salt of the naproxen undergo a quick and strong degradation fostered by the light and the heat, as fully documented by Douglas E. Moore et al. in Photochem. Photobiol., 47, 173-180, (1988).

Really, till now the use of the naproxen by injectable way was always carried out by dissolving the freeze-dried sodium salt of the naproxen, at the moment of the taking, by means of a vial containing the solvent liquid.

This kind of making and use obviously shows many drawbacks, the main of them being the risk of ambient contamination during the dissolution. Therefore it is certainly desirable to have available a single vial, containing the sodium salt of the naproxen already dissolved, which offers remarkable advantages like a greater easiness of manufacturing and a lowering of the operations necessary for the administration of the drug that brings to an easier use and therefore to lower risks of contamination.

Therefore the aim of the present invention consists in finding a system to make stable for a long period of time aqueous solutions containing the sodium salt of the naproxen also in the presence of unfavourable conditions of heat and light.

We discovered that by adding antioxidizing and radical scavanger chemical substances like, for instance, compounds containing sulphydryl, sulfide or disulfide groups, together with polyhydroxylic alcohols, to the aqueous solutions of the sodium salt of the naproxen, the stability of these aqueous solutions increases in a very remarkable manner. This stability becomes further more marked by packaging the vials or the medicine-bottles containing these stabylized solutions in suitable containers made by boxes of polystyrene or of an equivalent material, like for instance polyvinylchloride, covered with films that prevent the light radiations from interacting with the substances dissolved.

DESCRIPTION OF THE INVENTION

Aqueous injectable pharmaceutical formulations containing therapeutically effective amounts of naproxen sodium salt, a drug endowed with anti-inflammatory, analgesic and antipyretic activity, together with stabilizing agents and polyhydroxylic alcohols and, optionally, excipients like, for instance, local anaesthetics like the lidocaine base or lidocaine salts, preferably the hydrochloride, or mixtures thereof, are the object of the present invention.

A type of packaging where the containers of the vials or of the medicine-bottles are boxes of polystyrene or of an equivalent material, like, for instance, polyvinylchloride, covered by films that absorb the light radiations, is a further object of the present invention, equally with the scope to keep stable during the time the injectable solutions containing the sodium salt of the naproxen.

Also the pharmaceutical packages, as well as the relating preparings, coming from the packaging of the above mentioned formulations in the above mentioned boxes, are an object of the present invention.

The realization of the invention consists in adding an amount of stabilizing agents comprised between 0,25% and 5% in weight and an amount of polyhydroxylic alcohols comprised between 5% and 50% in weight and, optionally, some excipients like, for instance, local anaesthetics like lidocaine base or lidocaine salts, preferably the hydrochloride, or mixtures thereof, to an aqueous solution containing from 3% to 15% in weight of the sodium salt of the naproxen and in packaging the vials or the medicine-bottles in a box covered by a film that absorbs the light radiations.

In the formulations object of the present invention, the preferred dosage of the sodium salt of the naproxen is comprised between 200 and 1000 mg for each vial or medicine-bottle, the amount of the stabilizing agents between 10 and 300 mg and the amount of polyhydroxylic alcohols between 200 and 2000 mg.

Many chemical substances having antioxidizing and radical scavenger activity can be advantageously used as stabilizing agents.

Most of them contain solfur in the shape of sulfhydryl, sulfide or disulfide groups.

N-acetyl-L-cysteine, cysteine, cysteamine, cystamine, glutathione, imidazole and mixtures thereof are preferred among the stabilizing agents.

Many polyhydroxylic alcohols are suitable in order to obtain the desired results within the scope of the invention and propylene glycol, sorbitol, mannitol, xylitol, glycerol, inositol and mixtures thereof are the preferred ones.

Containers made by boxes of polystyrene or of an equivalent material, like for instance polyvinylchloride, covered by films made of various material, like, for instance, thermo-weldable films of aluminium, films made of plastic materials like polythene, cellophane, polyvinylchloride and polystyrene, transparent or opaque, and of many colors like, for instance, dark green, dark red, amber, brown or blue, are used for the packaging.

As it results from drawings 1, 2 and 3, which respectively represent the plan (FIG. 1), the side (FIG. 2) and the front (FIG. 3), the container of vials or medicine-bottles is made of a box of polystyrene or of an equivalent material, like for instance polyvinylchloride, in the shape of a parallelepiped (1) containing in its interior a series of division walls (2) which mark the limits of the lodgings (3) for the single vials or medicine-bottles, covered by a film (4) which absorbs the light radiations. Both the containers and the vials or the medicine-bottles can be of various dimensions; generally the number of the lodgings is comprised between 2 and 12 and the content of each single vial or medicine-bottle is comprised between 1 ml and 10 ml. In a preferred aspect of the invention, the packaging contains 6 vials having a volume of 4 ml.

The preparation of the injectable solutions takes place by dissolving the stabilizing agents in about ⅔ of the foreseen amount of water for injectable preparations and then by bringing the pH of the solution to a value comprised between 7.5 and 9.5 by means of a 10% (w/w) aqueous solution of sodium hydroxide or of 1N hydrochloric acid. The polyhydroxylic alcohol, the sodium salt of the naproxen and possible excipients like local anaesthetics like lidocaine base or salts of lidocaine, preferably the hydrochloride, or mixtures thereof, are added afterwards.

Subsequently the injectable solution is brought to the end desired volume, by contemporaneously checking the value of the pH by means of a possible addition of a 10% (w/w) aqueous solution of sodium hydroxide or of 1N hydrochloric acid, by adding water for injectable preparations and lastly it is sterilely filtered and put into the vials or the medicine-bottles in aseptic ambient.

The whole process for the preparation of the injectable solutions, comprised the final filling of vials or of medicine-bottles, is carried out under nitrogen atmosphere.

Said vials or medicine-bottles are then packaged in the above described boxes.

These packagings have been submitted to two kinds of stability tests both in comparison with samples without stabilizing agent and polyhydroxylic alcohol packaged in a container lacking of the film that absorbs the light radiations (comparison 1), and with samples packaged in a container made according to the present invention but without the stabilizing agent and the polyhydroxylic alcohol (comparison 2).

The first stability test is a thermostability test: the samples described in examples from 1 to 8 and the two comparison samples have been stored in a thermostatic stove at the temperature of 60° C. in the dark.

The second stability test is a photostability test: the samples described in examples from 1 to 10 and the two comparison samples have been exposed, in a suitable chamber, to the natural light, at a temperature ranging between about 20° C. and about 45° C.

Takings for the analytic control of the parameters necessary to establish the stability or instability of the solution under examination have been carried out at prearranged intervals of time. The investigated parameters are those that the experience showed to be representative of the likely reactions of degradation, exactly the clearness and the color.

As a matter of fact, the solution, because of the phenomena of degradation, goes from colorless to colored, the color darkening with the progress of the processes of degradation and subsequently it loses its clearness, it becomes opaque and, lastly, some solid substance precipitates.

The data of stability of the injectable solutions submitted to the test of thermostability are summarized in table 1, while the data of stability of the injectable injections submitted to the test of photostability to the natural light in chamber with a temperature comprised between about 20° C. and about 45° C. are summarized in table 2.

The choice of the natural light and of the range of temperature was made on the ground that this experimental condition better reflects the real condition in which the product can be during the normal use.

In the following tables 1 and 2, the color of the solutions was shown by means of letters corresponding to the classification of the colors according to the Pharmacopee Europeenne V, 6.2 (1980):

B = BRUN (BROWN)
JB = JAUNE BRUNATRE (YELLOW BROWN)
J = JAUNE (YELLOW)
R = ROUGE (RED)

The number of the color is decreasing at the increase of the intensity, i.e. number 1 represents the most intense coloring.

TABLE 1

Test of Thermostability

| SAMPLE | PARAMETER | TIME (days) 0 | 5 | 15 | 30 | 45 | 60 | 90 |
|---|---|---|---|---|---|---|---|---|
| Example 1 | appearance | clear | clear | clear | clear | clear | clear | clear |
| | color | colorless | colorless | colorless | colorless | colorless | colorless | colorless |
| Example 2 | appearance | clear | clear | clear | clear | clear | clear | clear |
| | color | colorless | colorless | colorless | colorless | colorless | colorless | colorless |
| Example 3 | appearance | clear | clear | clear | clear | clear | clear | clear |
| | color | colorless | colorless | colorless | colorless | colorless | colorless | colorless |
| Example 4 | appearance | clear | clear | clear | clear | clear | clear | clear |
| | color | colorless | colorless | colorless | colorless | colorless | colorless | colorless |
| Example 5 | appearance | clear | clear | clear | clear | clear | clear | clear |
| | color | colorless | colorless | colorless | colorless | colorless | colorless | colorless |
| Example 6 | appearance | clear | clear | clear | clear | clear | clear | clear |
| | color | colorless | colorless | colorless | colorless | colorless | colorless | colorless |
| Example 7 | appearance | clear | clear | clear | clear | clear | clear | clear |
| | color | colorless | colorless | colorless | colorless | colorless | colorless | colorless |
| Example 8 | appearance | clear | clear | clear | clear | clear | clear | clear |
| | color | colorless | colorless | colorless | colorless | colorless | colorless | colorless |
| Comparison 1 | appearance | clear | clear | clear | clear | opal. | opal. | opal. |
| | color | colorless | R6 | R4 | R4 | R3 | R3 | R2B3 |
| Comparison 2 | appearance | clear | clear | clear | clear | opal. | opal. | opal. |
| | color | colorless | R6 | R5 | R5 | R4 | R4 | R3B3 | opal. = opalescent

TABLE 2

Test of Photostability

| SAMPLE | PARAMETER | TIME (days) 0 | 5 | 15 | 30 | 45 | 60 | 90 |
|---|---|---|---|---|---|---|---|---|
| Example 1 | appearance | clear | clear | clear | clear | clear | clear | clear |
| | color | colorless | colorless | colorless | colorless | colorless | colorless | colorless |
| Example 2 | appearance | clear | clear | clear | clear | clear | clear | clear |

TABLE 2-continued

Test of Photostability

| SAMPLE | PARAMETER | TIME (days) | | | | | | |
|---|---|---|---|---|---|---|---|---|
| | | 0 | 5 | 15 | 30 | 45 | 60 | 90 |
| Example 3 | color | colorless | colorless | colorless | colorless | colorless | colorless | colorless |
| | appearance | clear | clear | clear | clear | clear | clear | clear |
| Example 4 | color | colorless | colorless | colorless | colorless | colorless | colorless | colorless |
| | appearance | clear | clear | clear | clear | clear | clear | clear |
| Example 5 | color | colorless | colorless | colorless | colorless | colorless | colorless | colorless |
| | appearance | clear | clear | clear | clear | clear | clear | clear |
| Example 6 | color | colorless | colorless | colorless | colorless | colorless | colorless | colorless |
| | appearance | clear | clear | clear | clear | clear | clear | clear |
| Example 7 | color | colorless | colorless | colorless | colorless | colorless | colorless | colorless |
| | appearance | clear | clear | clear | clear | clear | clear | clear |
| Example 8 | color | colorless | colorless | colorless | colorless | colorless | colorless | colorless |
| | appearance | clear | clear | clear | clear | clear | clear | clear |
| Example 9 | color | colorless | colorless | colorless | colorless | colorless | colorless | colorless |
| | appearance | clear | clear | clear | clear | clear | clear | clear |
| Example 10 | color | colorless | colorless | colorless | colorless | colorless | colorless | colorless |
| | appearance | clear | clear | clear | clear | clear | clear | clear |
| Comparison 1 | appearance | clear | clear | very opal. + precip. | very opal. + precip. | very opal. + precip. | very opal. + precip. | very opal. + precip. |
| | color | colorless | R5J5 | B6 | J6 | J6 | J6 | J6 |
| Comparison 2 | appearance | clear | clear | clear | clear | clear | clear | opal. |
| | color | colorless | R5B6 | R5B6 | R4B5 | R4B4 | R4B4 | R4B4 | opal = opalescent
precip = precipitate

The following examples are an illustration of the invention, but they are not to be considered as an its limitation.

EXAMPLE 1

50 Grams of N-acetyl-L-cysteine are dissolved, under nitrogen atmosphere, in 2600 ml of water for injectable preparations and then the value of the pH is brought to 8.5 by means of a 10% (w/v) aqueous solution of sodium hydroxide.

400 Grams of propylene glycol, 275 g of the sodium salt of naproxen and a mixture of lidocaine base and of lidocaine hydrochloride equivalent to 20 g of lidocaine, are added to the solution, while keeping it under stirring, always under nitrogen atmosphere, until complete dissolution.

The solution is then brought to the volume of 4000 ml by adding water for injectable preparations while contemporaneously keeping the value of the pH at 8.5 by means of a possible addition of a 10% (w/v) aqueous solution of sodium hydroxide.

The so obtained solution is sterilely filtered and lastly used to fill, in aseptic ambient under nitrogen atmosphere, 1000 vials having a volume of 4 ml which are packaged in containers of a shape analogous to that shown in FIGS. 1, 2 and 3 covered by a film of polythene of dark green color.

EXAMPLE 2

The preparation according to example 1 is repeated, by packaging in containers covered by a film of polythene of dark red color.

EXAMPLE 3

The preparation according to example 1 is repeated, by packaging in containers covered by a film of polythene of amber color.

EXAMPLE 4

The preparation according to example 1 is repeated, by packaging in containers covered by a film of aluminium.

EXAMPLE 5

The preparation according to example 1 is repeated, by packaging in containers covered by a film of polystyrene.

EXAMPLE 6

The preparation is carried out exactly as in example 1 with the only difference that 400 g of glycerol are used as polyhydroxylic alcohol instead of 400 g of propylene glycol.

EXAMPLE 7

The preparation is carried out exactly as in example 1 with the only difference that 400 g of sorbitol are used as polyhydroxylic alcohol instead of 400 g of propylene glycol.

EXAMPLE 8

The preparation is carried out exactly as in example 1 with the only difference that 400 g of xylitol are used as polyhydroxylic alcohol instead of 400 g of propylene glycol.

EXAMPLE 9

The preparation is carried out exactly as in example 1 with the only difference that 100 g of imidazole are used as stabilizing agent instead of 50 g of N-acetyl-L-cysteine. The pH is kept at the value of 8.5 by adding a sterile aqueous solution of 1N hydrochloric acid.

EXAMPLE 10

The preparation is carried out exactly as in example 1 with the only difference that 100 g of glutathione are used as stabilizing agent instead of 50 g of N-acetyl-L-cysteine.

What is claimed is:

1. A container for storing vials or medicine bottles which contain an aqueous injectable pharmaceutical formulation containing a therapeutically effective amount of the sodium salt of naproxen, a stabilizing agent and a polyhydroxylic alcohol, said stabilizing agent being a member selected from the group consisting of N-acetyl-L-cysteine, cysteine, cysteamine, cystamine, glutathione, imidazole and mixtures thereof, said polyhydroxylic alcohol being a member selected from the group consisting of propylene glycol, sorbitol, mannitol, xylitol, glycerol, inositol and mixtures thereof, said container having the shape of a parallelepiped and being made of polystyrene or polyvinyl chloride, said container having in the interior thereof a series of division walls, said walls marking the limits of lodgings for the vials or medicine bottles, said container being covered by a film which absorbs light radiation.

2. The container according to claim 1 wherein the material which forms the film is a thermo-weldable aluminum, a transparent or non-transparent plastic material which is polyethene, cellophane, polyvinylchloride or polystyrene.

3. The container according to claim 2 wherein said plastic material is dark green, dark red, amber color, brown or blue.

4. The container according to claim 1 wherein the formulation additionally contains lidocaine, lidocaine hydrochloride or a mixture thereof.

5. The container according to claim 1 wherein in said formulation the amount of the sodium salt of naproxen is between 3% and 15% by weight of the formulation, the amount of the stabilizing agent is between 0.25% and 5% and the amount of polyhydroxylic alcohol is between 5% and 50%.

6. The container according to claim 1 wherein a single dose of the pharmaceutical formulation contains from 200 mg to 1,000 mg of the sodium salt of the naproxen, from 10 mg to 300 mg of said stabilizing agent and from 200 mg to 2,000 mg of said polyhydroxylic alcohol.

7. The container according to claim 1 wherein said pharmaceutical formulation has a pH of 7.5–9.5.

* * * * *